US00PP11896P2

(12) United States Plant Patent
Boeder

(10) Patent No.: US PP11,896 P2
(45) Date of Patent: May 29, 2001

(54) CHRYSANTHEMUM PLANT NAMED 'TRUE YELLOW AT'

(75) Inventor: Mark Boeder, West Wittering (GB)

(73) Assignee: Cleangro Limited, West Sussex (GB)

( * ) Notice: Subject to any disclaimer, the term of this patent is extended or adjusted under 35 U.S.C. 154(b) by 0 days.

(21) Appl. No.: 09/209,857

(22) Filed: Dec. 11, 1998

(51) Int. Cl.[7] ..... A01H 5/00
(52) U.S. Cl. ..... Plt./289
(58) Field of Search ..... Plt./289

(56) References Cited

U.S. PATENT DOCUMENTS

P.P. 5,409 * 2/1985 Duffett ..... Plt./289
P.P. 5,995 * 5/1987 Duffett et al. ..... Plt./289
P.P. 7,955 * 8/1992 VandenBerg ..... Plt./289

* cited by examiner

*Primary Examiner*—Howard J. Locker
(74) *Attorney, Agent, or Firm*—Howrey Simon Arnold & White, LLP

(57) ABSTRACT

A new plant variety of Chrysanthemum producing yellow decorative-type flowers.

1 Drawing Sheet

BACKGROUND OF THE INVENTION

The present invention is directed to a new and distinct variety of Chrysanthemum *Dendranthema grandiflora*. The varietal denomination of the new Chrysanthemum is 'TRUE YELLOW AT'.

The new variety was a naturally occurring whole plant mutation which originated in a controlled cultivated planting of the variety known as 'About Time' (Application Ser. No. 08/316,947, abandoned). 'True Yellow AT' has been asexually reproduced by vegetative cuttings in Ventura County, Calif. and the distinguishing characteristics are retained through successive generations of asexual reproduction.

SUMMARY OF THE INVENTION

'True Yellow AT' is a pot-type Chrysanthemum plant variety having a flat capitulum form, and producing yellow decorative-type flowers.

COMPARISON WITH PARENT

The new variety produces yellow flowers whereas the parent 'About Time' produces coral pink flowers.

BRIEF DESCRIPTION OF ILLUSTRATION

The accompanying photograph shows typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. in the month of April. 'True Yellow AT' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the shelf life of 'True Yellow AT' is about 20 days and a response time of about 8.5 weeks. One application of growth retardant B9 at about 2500 ppm was used with plants described. Useful growing conditions include night temperatures of about 18°–20° C., day temperatures of about 20 –30° C.

Plant:
- *Habit.*—Upright, herbaceous perennial.
- *Height.*—About 28 cm.
- *Number of breaks from pinch.*—About 4 to 5.
- *Length of lateral branches.*—About 21 cm.
- *Stem color.*—Near 138A.

Foliage:
- *Leaf arrangement.*—Alternate.
- *Number of leaves per lateral branch.*—About 11 fully expanded leaves.
- *Leaf size.*—Length: About 7.2 cm. Width: About 4.6 cm.
- *Leaf shape.*—Ovate.
- *Attachment.*—Petioled.
- *Leaf apex.*—Acute.
- *Base.*—Tapered, truncate.
- *Margin.*—Palmately lobed.
- *Aspect.*—Slightly undulate.
- *Surface.*—Top: Lightly pubescent. Bottom: Pubescent.
- *Venation.*—Net, mid vein prominent on underside. Color: Upper side: Near 137C. Underside: Near 146C.
- *Petiole.*—Length: About 1.7 cm. Color: Near 145A.

Color:
- *Mature leaf.*—Top: Near 137A. Bottom: Near 137B.
- *Young leaf.*—Top: Near 137A. Bottom: Near 137C.

Bloom:
- *Inflorescence form.*—Cyme.
- *Flower form.*—Decorative.
- *Number of blooms per branch.*—About 6.
- *Diameter of fully expanded bloom.*—About 7.5 cm.
- *Depth of fully expanded bloom.*—About 1.5 cm.
- *Sepal number.*—About 60. Color: Near 137C. Length About 1 cm. Width: About 0.6 cm.

*Peduncle.*—Length: Terminal: About 3.6 cm. Lateral: About 7.7 cm. Habit: Straight. Surface: Pubescent. Color: Near 137C.

*Flower bud* (*when just showing color*).—Color: Near 7C. Diameter: About 1 cm. Height: About 1 cm. Shape: Spherical.

*Ray florets.*—Number per flower: About 180. Texture: Matte. Shape: Oblanceolate. Apex: About 3 to 4 obtuse, irregular lobes. Base: Tapered. Margin: Entire. Aspect: Slightly incurved, undulating. Length: About 3.7 cm. Width: About 1.4 cm.

*Disc florets.*—Number per flower: About 5. Texture: Shiny. Shape: Cylindric. Length: About 0.4 cm. Width: About 0.1 cm.

*Fragrance.*—Faint.

Flower color:

*General flower coloration.*—Yellow decorative.

*Ray florets, top side.*—Immature: Near 7B. Mature: Near 7A. Fading: Near 8A.

*Ray floret, under side.*—Immature: Near 8A. Mature: Near 8B. Fading: Near 8C.

*Disc florets.*—Immature: Near 154B. Mature: Near 1B. Fading: Near 9B.

Changes as the flower ages: Flower color fades very slightly; flower form remains flat.

Reproductive organs:

*Ray florets.*—Pistillate. Stigma shape: 2 branched. Stigma color: Near 2B. Style length: About 0.5 cm. Style color: Near 154 C.

*Disc florets.*—Stigma shape: Linear. Stigma color: Near 1A. Style length: About 0.3 cm. Style color: Near 1D. Stamen number: About 5. Anther length: About 0.2 cm. Pollen color: Near 13B. Pollen quantity: Moderate.

What is claimed is:

1. A new and distinct Chrysanthemum plant of the variety substantially as herein shown and described.

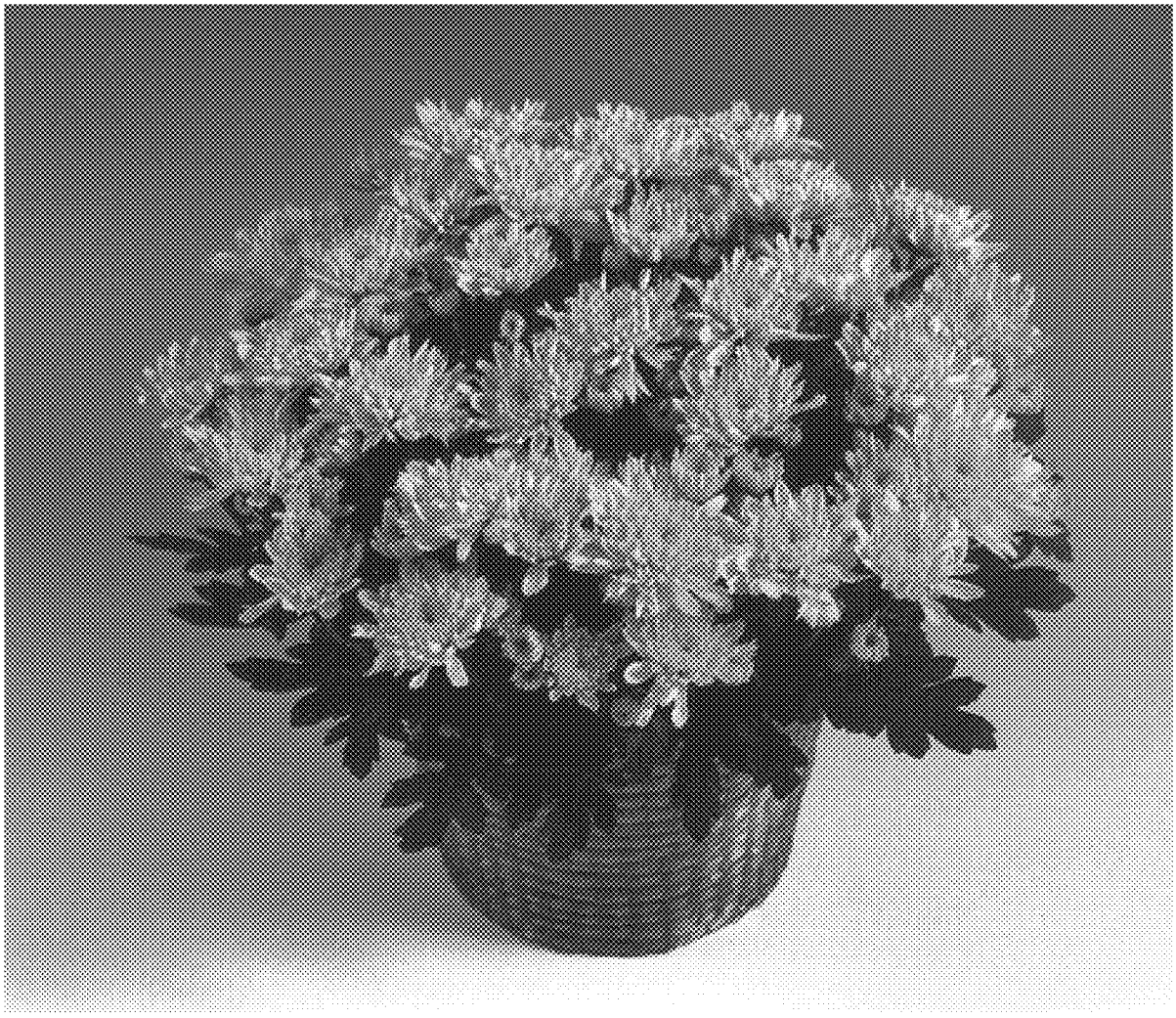

* * * * *